(12) United States Patent
Colquhoun et al.

(10) Patent No.: US 8,998,917 B2
(45) Date of Patent: Apr. 7, 2015

(54) INSTRUMENT ASSEMBLY FOR USE IN KNEE JOINT REPLACEMENT SURGERY

(75) Inventors: Callum Colquhoun, Belgrave (AU); Michael Rock, Leeds (GB)

(73) Assignee: Depuy International Ltd., Leeds (GB)

( * ) Notice: Subject to any disclaimer, the term of this patent is extended or adjusted under 35 U.S.C. 154(b) by 1888 days.

(21) Appl. No.: 12/088,756

(22) PCT Filed: Sep. 21, 2006

(86) PCT No.: PCT/GB2006/003503
§ 371 (c)(1),
(2), (4) Date: Dec. 15, 2008

(87) PCT Pub. No.: WO2007/036694
PCT Pub. Date: Apr. 5, 2007

(65) Prior Publication Data
US 2009/0138021 A1 May 28, 2009

(30) Foreign Application Priority Data
Sep. 30, 2005 (GB) .................................. 0519832.0

(51) Int. Cl.
*A61B 17/02* (2006.01)
*A61B 17/15* (2006.01)
(Continued)

(52) U.S. Cl.
CPC ............. *A61B 17/025* (2013.01); *A61B 17/155* (2013.01); *A61B 17/157* (2013.01); *A61B 2017/0268* (2013.01); *A61B 2019/461* (2013.01)

(58) Field of Classification Search
CPC .............................................. A61B 2017/0268

USPC .................... 606/86 R, 87, 88, 90, 102, 105; 600/210, 214, 219–222; 81/302, 424
See application file for complete search history.

(56) References Cited

U.S. PATENT DOCUMENTS 3,750,652 A * 8/1973 Sherwin .......................... 606/90
4,501,266 A * 2/1985 McDaniel ....................... 606/90
(Continued)

FOREIGN PATENT DOCUMENTS

DE 10335410 A1 2/2005
EP 979636 4/2009
(Continued)

OTHER PUBLICATIONS

PCT Written Opinion, 5 pages.
(Continued)

*Primary Examiner* — Michael T Schaper

(57) ABSTRACT

An instrument assembly for use in knee joint replacement surgery is provided including a base instrument having a tibial plate, a femoral plate, a tibial arm having a plate end and a control end, a femoral arm having a plate end and a control end, wherein the femoral plate is rotatably fastened to the plate end of the femoral arm. The assembly also includes a distractor mechanism configured to act between the tibial arm and the femoral arm at a point between their respective plate ends and control ends by which the distance between the plate ends of the arms can be adjusted and an ancillary instrument mountable on the base instrument and configured such that the position of the ancillary instrument relative to the tibial plate is fixed during subsequent steps in the knee replacement procedure, while the knee joint is distracted as a result of forces applied across the joint between the tibial plate and the femoral plate.

12 Claims, 3 Drawing Sheets

(51) Int. Cl.
*A61B 17/17* (2006.01)
*A61B 19/00* (2006.01)

(56) References Cited

U.S. PATENT DOCUMENTS

| | | | | |
|---|---|---|---|---|
| 4,566,448 | A * | 1/1986 | Rohr, Jr. | 606/88 |
| 4,898,161 | A * | 2/1990 | Grundei | 606/105 |
| 4,938,762 | A * | 7/1990 | Wehrli | 606/88 |
| 5,431,653 | A * | 7/1995 | Callaway | 606/90 |
| 5,540,696 | A * | 7/1996 | Booth et al. | 606/88 |
| 5,649,929 | A | 7/1997 | Callaway | |
| 5,800,438 | A * | 9/1998 | Tuke et al. | 606/90 |
| 5,911,723 | A * | 6/1999 | Ashby et al. | 606/88 |
| 5,931,777 | A * | 8/1999 | Sava | 600/213 |
| 6,022,377 | A * | 2/2000 | Nuelle et al. | 606/90 |
| 6,159,217 | A * | 12/2000 | Robie et al. | 606/88 |
| 6,261,296 | B1 * | 7/2001 | Aebi et al. | 606/90 |
| 6,648,896 | B2 * | 11/2003 | Overes et al. | 606/90 |
| 7,156,853 | B2 * | 1/2007 | Muratsu | 606/102 |
| 8,137,361 | B2 * | 3/2012 | Duggineni et al. | 606/102 |
| 2002/0123754 | A1 | 9/2002 | Holmes | |
| 2002/0156480 | A1 | 10/2002 | Overes | |
| 2002/0165550 | A1 * | 11/2002 | Frey et al. | 606/85 |
| 2003/0225416 | A1 * | 12/2003 | Bonvallet et al. | 606/105 |
| 2004/0106927 | A1 | 6/2004 | Ruffner | |
| 2004/0122441 | A1 * | 6/2004 | Muratsu | 606/102 |
| 2004/0249387 | A1 * | 12/2004 | Faoro | 606/88 |
| 2005/0059980 | A1 * | 3/2005 | Overes | 606/102 |
| 2005/0085920 | A1 | 4/2005 | Williamson | |
| 2005/0177173 | A1 | 8/2005 | Aebi et al. | |
| 2006/0074432 | A1 * | 4/2006 | Stad et al. | 606/90 |
| 2007/0239157 | A1 * | 10/2007 | Guillaume | 606/60 |

FOREIGN PATENT DOCUMENTS

| | | | | |
|---|---|---|---|---|
| GB | 2198647 | A | 6/1988 | |
| WO | WO 00/19911 | A | 4/2000 | |
| WO | WO 0185038 | A1 * | 11/2001 | A61B 17/15 |
| WO | WO 02/071924 | A2 | 9/2002 | |
| WO | WO 02/087466 | A | 11/2002 | |
| WO | WO 03/084412 | A | 10/2003 | |
| WO | WO 03084412 | A1 * | 10/2003 | A61B 17/15 |

OTHER PUBLICATIONS

International Search Report, dated Dec. 11, 2006, 4 pages.
UK Search Report, dated Jan. 25, 2006, 4 pages.
International Search Report, dated Dec. 8, 2006, 4 pages—related art.
UK Search Report, dated Jan. 25, 2006, 4 pages—related art.
LCS Complete Mobile-Bearing Knee System, Surgical Technique, 3M1001, 0611-63-050 (Rev. 2), 2001 (41 pages).
AMK Congruency Instrument System, Surgical Technique, 2.7M1198, 0612-76-000, 1997 (16 pages).
Knee Balancer Complementing P.F.C. Sigma and LCS Complete EGF Instrumentation, Reference Guide and Surgical Technique, 4M0703, 0612-21-500, 2003 (15 pages).

* cited by examiner

INSTRUMENT ASSEMBLY FOR USE IN KNEE JOINT REPLACEMENT SURGERY

This invention relates to an instrument assembly for use in a knee joint replacement surgery.

It is important to locate components of a knee joint prosthesis accurately relative to the patient's tibia and femur in order for the implanted joint prosthesis to function reliably. Accurate location of the prosthesis components relative to the bone depends on accurate preparation of the tibia and femur, in particular that the bones are resected accurately.

It is common for the tibia to be resected first. Techniques for locating the tibial resection plane are well known; a suitable technique might involve for example use of an extra-medullary alignment rod.

Preparation of a femur for implantation of the femoral component of a knee joint prosthesis generally involves performing distal, anterior, posterior, anterior chamfer and posterior chamfer cuts. Factors which should be taken into account when determining the location of these cuts include the spacing between the femur and tibia that is required to achieve appropriate tension in the joint soft tissue, with the joint in both flexion and extension. The first cut that is performed on the femur is generally the distal cut or the anterior cut. It can be desirable to determine the plane or the orientation or both of these cuts with reference to the resected tibia.

Location of the orientation or the plane of a femoral cut with reference to the resected tibia requires that the medial and lateral ligaments which span the joint are placed under tension. Devices for tensioning the ligaments are known, for example as disclosed in EP-A-979636 and U.S. Pat. No. 4,566,448. U.S. Pat. No. 5,431,653 and U.S. Pat. No. 5,649,929 relate to ligament tensioning devices which comprise two pivotally interconnected arms. Each of the arms has a plate at one end for engaging the articulating surfaces of the femur and tibia respectively. The plates on the arms can be forced apart to apply tension to across the joint by relative pivotal movement of the arms. A locking device between the arms can lock the plates in a spaced apart position to maintain the joint ligaments under tension.

The arms used in the devices disclosed in U.S. Pat. No. 5,431,653 and U.S. Pat. No. 5,649,929 enable tension to be across the joint but the instrument has to be removed from the joint before subsequent steps in the procedure can be performed because it obstructs access to the joint space.

The present invention provides an instrument assembly for use in knee joint replacement surgery, comprising a base instrument with tibial and femoral arms extend from respective plates within the joint space generally medially or laterally of the joint, and an ancillary instrument which can be mounted on the base instrument.

Accordingly, in one aspect, the invention provides an instrument assembly for use in knee joint replacement surgery, comprising a base instrument which comprises:

a base instrument that comprises:
  a tibial plate;
  a femoral plate;
  a tibial arm having a plate end and a control end, wherein the tibial plate is fastened to the plate end of the tibial arm at its anterior edge, and wherein, when the tibial plate contacts the tibia, the tibial arm is configured to extend from the tibial plate generally medially or laterally of the knee joint;
  a femoral arm having a plate end and a control end, wherein the femoral plate is rotatably fastened to the plate end of the femoral arm, and wherein, when the femoral plate contacts the femur, the femoral arm extends from the femoral plate generally aligned with the tibial arm; and
  a distractor mechanism configured to act between the tibial arm and the femoral arm at a point between their respective plate ends and control ends by which the distance between the plate ends of the arms can be adjusted, and
an ancillary instrument mountable on the base instrument and configured such that the position of the ancillary instrument relative to the tibial plate is fixed during subsequent steps in the knee replacement procedure, while the knee joint is distracted as a result of forces applied across the joint between the tibial plate and the femoral plate.

The ancillary instrument will generally be one whose position relative to the tibial resection plane should be controlled. For example the instrument might be used to measure the distance from the tibial resection plane to the femur to enable the correct selection of joint prosthesis components to ensure appropriate ligament tension. Such an instrument might include a probe for contacting the femur to measure the gap between the tibia and the femur.

The ancillary instrument might have a slot formed in it for receiving the blade of a saw or other cutting device. Such an instrument can be used to define the plane for resecting the femur.

The ancillary instrument might be a pin guide which has at least one hole extending through it to define the location for a hole which is to be prepared in the femur. The pin guide might have a slot formed in it for receiving the blade of a saw or other cutting device. Holes which are located using the pin guide might be used for fastening another cutting guide instrument (with a slot for receiving the blade of a saw or other cutting device) to the femur.

The instrument assembly of the invention has the advantage that ancillary instruments can be mounted conveniently relative to the resected tibia, and can be used to perform procedures on the knee joint, while tension is applied across the joint by means of the plate and arm assembly of the base instrument. This is made possible by the fact that the arms by which tension is applied across the joint extend generally in the medial-lateral direction. The extension of the arms generally in the medial-lateral direction can mean that obstruction of access to the joint space anteriorly of the joint by the arms is minimized. Furthermore, the size of the incision through which the plates of the base instrument are inserted into the joint space can be made smaller than is required for certain other joint tensioning instruments. Significantly, the extension of the arms generally in the medial-lateral direction means that tension can be applied across the joint using the base instrument while the patella lies in or close to its anatomic position. In particular, it will often not be necessary to displace (sublux) the patella significantly or to evert it in order to fit the plates into the space between the tibia and the femur. This provides the advantage that the procedure can be performed through a smaller incision that might be necessary if the patella is to be subluxed or everted. It also means that forces that are applied across the joint by ligaments that are connected to the patella do not include non-anatomic medial and lateral components. Accordingly, forces applied by patella ligaments do not affect tension in the medial and lateral ligaments.

It will be appreciated that the advantages referred to above can be achieved obtained when the medial and lateral arms do not extend directly along or parallel to the medial-lateral axis. The portion of the arms closest to the joint will generally extend close to the medial-lateral axis. However, it might be that the angle between the medial-lateral axis and one or each of the arms is greater than 0E, in the anterior-posterior direction or in the superior-inferior direction or both. The advantages can be obtained when the angle between the axis and at least a portion of one or each of the arms is 10E or more, for example at least about 20E, or at least about 30E.

The use of the plate and arm assembly of the base instrument can also allow a point of reference for subsequent procedural steps to be established quickly and easily compared with other techniques which might require steps such as drilling into bone and fixing reference instruments by means of pins or screws or both.

Preferably, the ancillary and base instruments have complimentary formations of a spigot and socket assembly which can be used to connect the instruments to one another. Preferably, the spigot is a snug fit in the socket so that play between the base and ancillary instruments is minimized. It can be preferred for the spigot to be in the form of a plate and the socket to be in the form of a slot in which the plate can be received. Preferably, the width of the slot is at least about 20 mm, more preferably at least about 25 mm, for example at least about 30 mm. Preferably, the depth of the slot is at least about 8 mm, more preferably at least about 10 mm, for example about 12 mm. Preferably, the height of the slot is at least about 1.5 mm, more preferably at least about 2.0 mm, for example about 2.5 mm.

The depth of the plate which fits into the slot can be greater than the depth of the slot when the slot is open at its opposite end, so that the plate protrudes from the slot when fully inserted.

The thickness of the plate should be only slightly less than the height of the slot, so that it is a tight sliding fit in the slot, allowing the plate to be slid smoothly into the slot but so that play between the plate and the slot is minimized.

It can be preferred for the width of the plate to be less than the width of the slot to allow the position of the plate relative to the slot, along the axis of the arm, to be changed slightly by sliding the plate in the slot. This can enable the position of an ancillary instrument relative to the knee joint to be adjusted generally in the medial lateral direction.

It will often be preferred that the spigot and socket of the assembly lie on an axis which is approximately parallel to the plane that is to the face of the tibial plate which contacts the resected tibia.

It will generally be preferred for the socket to be provided on the base instrument and the spigot to be provided on the ancillary instrument. This has the advantage that the profile of the base instrument is minimized.

Preferably, the formation of the spigot and socket assembly which is provided on the base instrument is provided on the tibial arm. The formation will generally be provided close to the tibial plate.

The tibial plate will generally be fastened rigidly to the tibial arm. It can be permanently connected to the tibial arm, for example by means of appropriate fasteners, or by welding or brazing or other bonding techniques. The tibial plate and the tibial arm can be made as a single component, for example by casting or by machining.

Preferably, the distractor mechanism comprises a pivot by which the tibial and femoral arms are connected to one another at a point between their plate and control ends so that pivotal movement of the femoral arm relative to the tibial arm to reduce the distance between their control ends causes the distance between their plate ends to increase. The portions of the tibial and femoral arms between the pivot and the control ends can be gripped by a user as handles, to apply a distracting force to the tibia and femur. The arms can cross one another at the pivot in the manner of a pair of scissors. However, it will often be preferred that arms do not cross, with at least one of them being cranked between the pivot and each of its plate and control ends. Preferably, the arm which is cranked in this way has its respective plate fastened to it in such a way that it can rotate relative to the arm so as to minimize differences in the force that is applied across the medial and lateral compartments of the joint. Preferably, the other arm is approximately straight, at least between the pivot and the plate end. Preferably, the plate which is provided on the straight arm is fastened rigidly to the arm so that it does not rotate.

The location of the pivot relative to the plate and control ends of the arms will be selected to provide an appropriate mechanical advantage during operation of the base instrument to apply force between the femur and tibia. It will often be preferred for the pivot to be located close to the midpoint of the tibial arm so that the mechanical advantage is close to 1:1, and so that the force that is applied to the instrument at the control ends of the arms is similar to the force that is applied by the instrument to the patient's joint at the plate ends of the arms.

Other distractor mechanisms can be used in the base instrument. For example, one of the arms might be connected to a rack and the other arms might be connected to a pinion. The rack and pinion assembly can be used to move one arm relative to the other, for example generally as taught in US-A-2004/0122441. Subject matter disclosed in that document is incorporated in the specification of this application by this reference.

Preferably, the base instrument includes a device for locking the tibial and femoral arms against the relative movement between them which involves reduction of the distance between their plate ends. The locking device can facilitate use of the base instrument to provide a mounting point for the ancillary instrument, providing a point of reference relative to the resected tibia. For example, the locking device might include a ratchet mechanism. A suitable ratchet mechanism might include a toothed rack which fastened to one of the plate arms, is engaged by a projection on the other arm. Another suitable locking device might include a threaded shaft and a nut which engages the shaft, as used in the device which is disclosed in U.S. Pat. No. 5,649,929. Subject matter disclosed in that document is incorporated in the specification of this application by this reference. The base instrument can also include a biasing device which acts on the tibial and femoral arms so as to reduce the distance between their plate ends.

Preferably, the femoral plate is able to rotate relative to the femoral arm so that differences in the forces that are applied across the medial and lateral compartments of the joint can be minimized. This can allow a surgeon to assess alignment of the planes on which the femur and the tibia are resected when the medial and lateral ligaments are placed under tension, and to make such corrections as might be appropriate, for example by further resection or by selective ligament release. The use of the base instrument of the invention to place the joint under tension has the advantage that the patella can remain in or close to its anatomic position and therefore does not affect significantly the relative tensions in the medial and lateral ligaments.

In a preferred construction, the femoral plate can be fastened to the femoral arm by means of a pin which extends from the femoral arm approximately along the anterior-posterior axis, and in which the femoral plate can rotate about the pin. The femoral plate can have a pair of recesses formed in it in which the femoral condyles can be located, particularly when movement of the femoral plate relative to the tibial plate by the action of the distractor mechanism is restricted to movement perpendicular to the plane of the resected tibia and does not include any component of movement along the medial-lateral axis. Such recesses can help to retain the femoral plate in contact with the condyles, possibly during flexion of the joint. It is an advantage of the instrument of the invention that it can be used to apply force across a knee joint during flexion, enabling procedures to be performed on the joint in both extension and flexion. For example, changes in the spacing between the tibia and the femur during flexion can be monitored.

The instrument assembly of the invention can be made from materials which are known for use in surgical instruments. Suitable metals include certain stainless steels. It can be preferred for the weight of the plate arms at least to be minimized. With this in mind, it can be preferred for one or both of the plate arms to be made from a polymeric material. Polymeric materials that are appropriate for use in the manufacture of surgical instruments are known. They include for example fiber reinforced resin materials, such as carbon fiber epoxy resins.

The components of the assembly of the invention should be constructed so that they can be disassembled easily for cleaning, at least if they are intended for multiple use. Design features which meet this requirement are known from other instruments.

Embodiments of the invention will now be described by way of example with reference to the accompanying drawings, in which.

Figure 1:
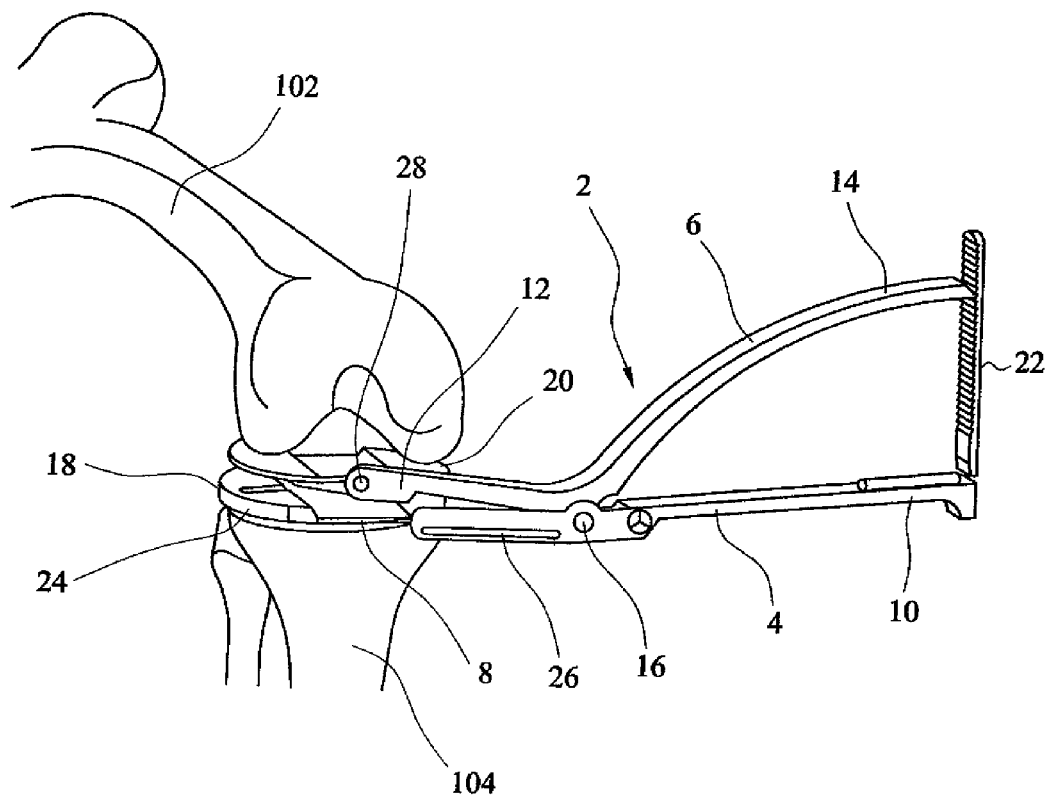
FIG. 1 is a front view of a femur and a tibia, with a base instrument according to the invention located between the femur and the tibia.

Referring to the drawings, FIG. 1 shows the base instrument 2 of an instrument assembly according to the invention, which comprises a tibial arm 4 and a femoral arm 6. The tibial arm includes a plate end 8 and a control end 10. The femoral arm includes a plate end 12 and a control end 14. The arms are connected to one another at a fulcrum, provided by a pivot pin 16. The pin extends through aligned holes in the arms (not shown) in an arrangement similar to what might be found in for example a hinge.

As can be seen in FIG. 1, the tibial arm is essentially straight, and the femoral arm is cranked towards the control end.

A tibial plate 18 is provided at the plate end of a tibial arm 8. A femoral plate 20 is provided at the plate end of a femoral arm 10.

The connection between the arms at the fulcrum is such that movement of the femoral arm relative to the tibial arm so as to reduce the distance between the control ends of the arms causes the distance between the plate ends to increase. Similarly, movement of the femoral arm relative to the tibial so as to increase the distance between the control ends of the arms causes the distance between the plate ends to decrease.

The plates are arranged on their respective arms such that the plates can be inserted into the space between the femur 102 and the tibia 104 through an anterior incision, and so that the arms extend from the incision in a direction which is generally laterally of the joint. The arms need not extend exactly parallel to the medial lateral axis. For example, the angle in the plane of the medial lateral axis between the axis and the direction in which the arms extend (measured at the plate end of the tibial arm) might be as much as 30E or more, for example about 40E. However, by arranging the arms so that they extend generally in this direction, the base instrument can be left with the plates within the joint space, and the arms do not interfere significantly with the performance of subsequent stages of the procedure. It can be a matter of surgeon choice as to whether the arms extend medially or laterally.

Figure 2:
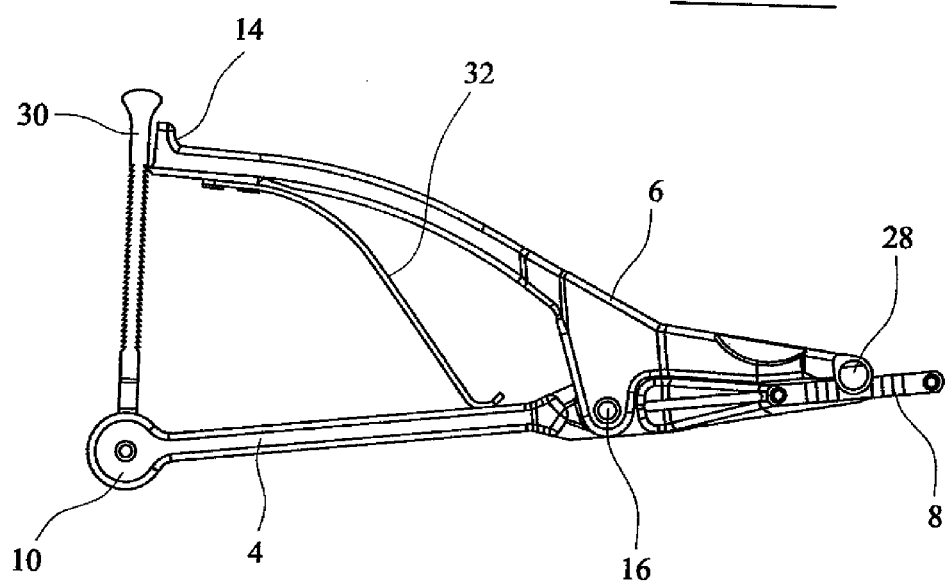
FIG. 2 is an enlarged view of the control ends of the arms of the base instrument which is shown in FIG. 1.

A ratchet stay 22 is provided at the control end 10 of the tibial arm 4. The stay is pivotally connected to the tibial arm so that it can be swung between an operative position (as shown in FIG. 1) in which it extends between the tibial arm and the femoral arm so that it engages the end of the femoral arm 6, and a disengaged position. The pivoting connection between the stay and the tibial arm is bistable biased, towards the control end of the femoral arm when in or close to its operative position, and away from the control end of the femoral arm when disengaged from the femoral arm. This can be achieved by means of a cam at the root of the stay and a sprung cam follower (not shown) within the tibial arm. FIG. 2 shows the ratchet stay in greater detail. The stay 30 has a toothed rack on the surface which faces towards the pivot pin 16. The control end 14 of the femoral arm 6 is formed as a sharpened blade which can fit between the teeth of the rack. A leaf spring 32 is provided on the femoral arm towards its control end, acting between it and the tibial arm to urge them apart. Movement of the control ends of the arms away from one another is restricted by engagement of the blade on the control end of the femoral arm on the ratchet stay.

The base instrument 2 can be used to distract a patient's knee joint. This can be achieved by inserting the tibial and femoral plates 8, 12 into the space between the resected tibia and the femur while the plate ends of the arms are close together and the control ends of the arms are spaced apart. The joint can be distracted by applying force to the arms to close the space between their control ends, against the force exerted between the control ends of the arms by the spring. The displacement of the arms is then locked by means of the ratchet stay 22.

The tibial plate 18 is integral with the tibial arm at its plate end. The integral connection between the plate and the arm means that the plate cannot be moved relative to the arm. This can be achieved by machining the plate and the arm from a single piece of material. It can also be achieved by fastening separately formed plate and arm to one another, for example by means of appropriate clips or fasteners, or by techniques such as welding.

The tibial plate has a planar inferior surface 24 which can fit on the surface of the resected tibia. The tibial plate can have formations (not shown) on its inferior surface to reduce the likelihood of unwanted relative lateral movement between the plate and the resected surface of the tibia. For example, the plate can be provided with pin-like or flange-like projections which are sharpened so that they can penetrate the surface of the tibia.

The tibial arm 4 has a slot 26 formed in it towards its plate end.

The femoral plate 20 is fastened to the femoral arm by means of a pin 28 which passes through a hole in the femoral arm and into a bore in the femoral plate. The plate 20 is able to rotate about the pin 28 relative to the femoral arm 6.

The femoral plate 20 has a pair of concave recesses formed in its superior surface, in which the condyles can be received.

Figure 3:
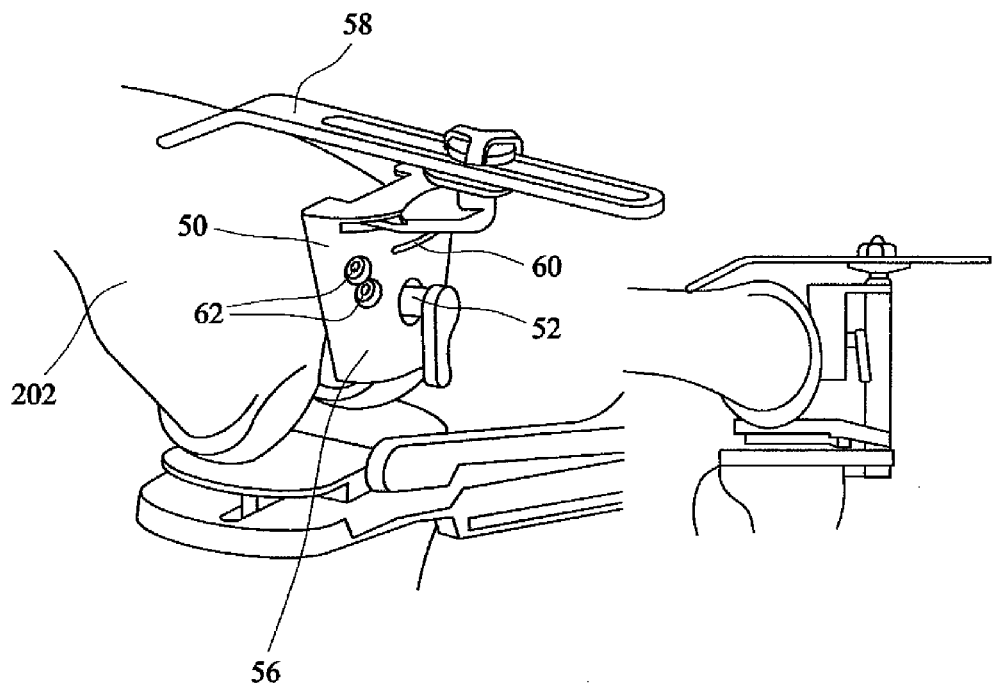
FIG. 3 is a side view (along the medial lateral axis) of a device for determining the appropriate height for the anterior femur cut relative to the tibial arm of the base instrument.

FIG. 3 shows an instrument 50 which can be used to locate the plane of the anterior cut of the femur 202 relative to the plane of the resected tibia. This procedure is carried out with the knee in flexion with an angle between the femoral and tibial axes of about 90E. The instrument comprises an intramedullary rod 52 and a cutting block 56 which can slide on the rod along the anterior-posterior axis. The instrument includes a stylus 58 which is fastened to the top of the cutting block. The stylus has a slot in it, to enable it to slide on a fastening pin. The pin is sprung loaded and the resulting frictional forces between the stylus and the plate restrict relative movement between the stylus and the block (as in other knee instruments such as that sold by DePuy International Limited under the trade mark LCS Completion).

The anterior cutting block has a saw cut slot 60 and fixation holes 62 (which can receive bone fastening pins) provided in it. The cutting block 56 is able to slide along the anterior-posterior axis. The appropriate position of the cutting block along the anterior-posterior axis is determined using the stylus, by positioning the tip of the stylus so that it contacts the anterior cortex. This involve moving the stylus relative to the cutting block so that its tip extends beyond the end of the condyle bearing surface. It then involves moving the cutting block posteriorly until the tip of the stylus contacts the femoral anterior cortex. The relationship between the dimensions of the stylus and the cutting block are then such that the plane defined by the saw cut slot 60 is appropriate to enable a femoral component to be fitted to the prepared femur.

Figure 4:
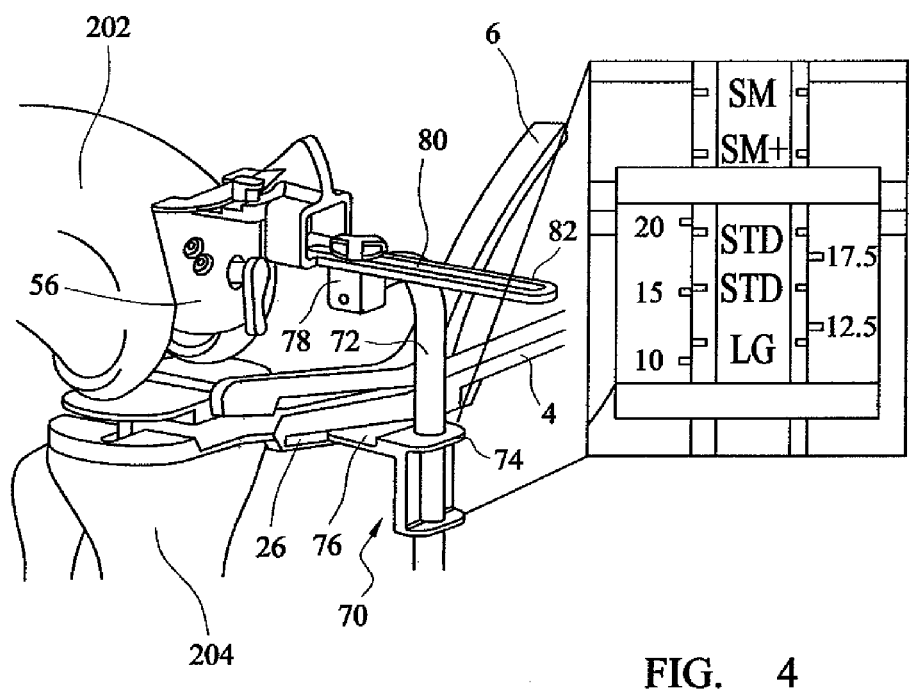
FIG. 4 is an isometric view of a device for measuring the gap between the tibia and the femur when the joint is in flexion.

FIG. 4 shows an ancillary instrument 70 which can be used to orientate the cutting anterior cutting block and to measure measuring the gap between the tibia 204 and the femur 202 when the knee joint is in flexion with an angle between the femoral and tibial axes of about 90E. The instrument comprises a shaft 72 and a bracket 74 having aligned openings in which the shaft can be received in a sliding fit. The bracket has a plate 76 extending from it. The plate is dimensioned to fit into the slot 26 in the tibial arm. The shaft is cranked towards its upper end so that the upper end 78 of the shaft is located in front of the femur, generally in line with the femoral axis.

An adjustable arm 80 has an elongate slot 82 formed in it. The arm is connected to the shaft 72 at its upper end 78 by means of a threaded screw which passes through the slot in the arm. The cutting block 56 can be connected to the arm 80.

In use, the anterior-posterior position of the cutting block 56 is determined as described above with reference to FIG. 3. The cutting block is then connected to the adjustable arm 80 while the base instrument is located between the femur and the tibia, and a force is applied to the joint as described above, and while the plate 76 is inserted in the slot 26 in the tibial arm 4.

When the anterior cutting block 56 and the arm 80 are connected to one another, a scale on the shaft 72, in a window in the bracket 74, provides an indication of the distance between the tibia 204 and the femur 202. This can be used in the selection of the size of the component of the knee joint prosthesis which is to be fitted to the patient's femur in the joint replacement procedure.

Figure 5:
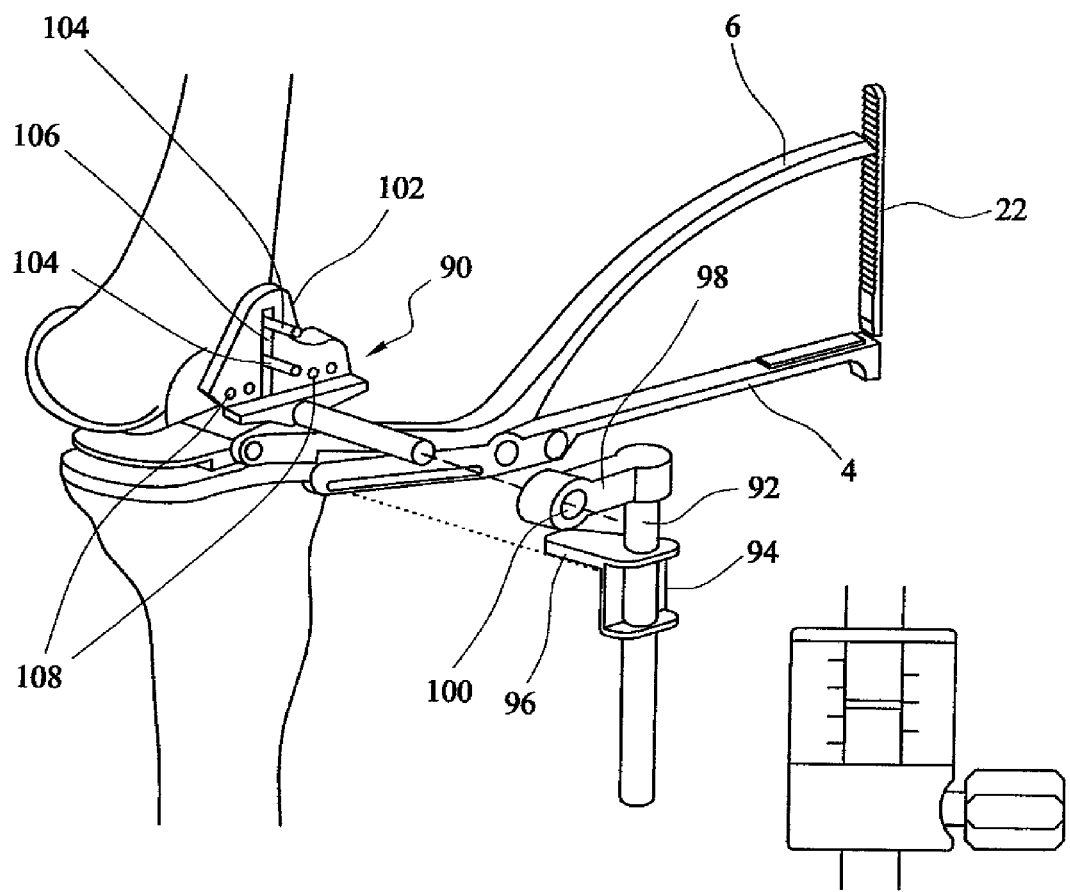
FIG. 5 is an isometric view of a device for locating a distal cutting guide on the femur relative to the tibial arm of the base instrument, according to the desired gap between the tibia and the femur when the joint is in extension.

FIG. 5 shows an ancillary instrument 90 for locating a distal cutting block on the femur according to the desired spacing between the resected tibia and resected femur (as determined using the flexion gap measuring instrument 70 described above with reference to FIG. 4) when the knee joint is extension, that is with the angle between the femoral and tibial axes being about 180E. The instrument comprises a shaft 92 and a bracket 94 having aligned openings in which the shaft can be received in a sliding fit. The bracket has a plate 96 extending from it. The plate is dimensioned to fit into the slot 26 in the tibial arm.

The shaft 92 has a transverse link 98 at its upper end, with a bore 100 extending through it at the end which is remote from the shaft. The dimensions of the transverse link are such that the axis defined by the bore is directed approximately towards the notch between the condyles when the plate 96 is inserted in the slot 26 in the tibial arm.

The instrument 90 includes an indicator block 102 which can be used to define the locations of fixation pins for a distal cutting block. The instrument enables the position of the distal cutting block to be determined along the mechanical axis of the femur. The mechanical axis is determined in a separate procedure as is known conventionally in knee surgery (for example, as with the instrument set sold by DePuy International Limited under the trade mark LCS Completion), and defined using a pair of pins 104. The indicator block 102 has a locator slot 106 formed in it through which the pins 104 can extend so that the block can slide relative to the femur on the pins, along the mechanical axis.

The indicator block includes a transverse shaft 106 which extends generally perpendicular to the mechanical axis of the femur, into the bore 100 in the transverse link 98. In this way, the position of the indicator block 102 relative to the femur can be controlled by movement of the shaft 92 in the bracket 94. The measurement obtained using the flexion gap measuring instrument 70 can be used to identify the appropriate position of the shaft in the bracket, and therefore of the indicator block relative to the femoral condyles. When the indicator block has been positioned appropriately along the mechanical axis of the femur, the position is marked using locator pins which are implanted in the femur through positioning holes 108. These locator pins can be used subsequently to locate a distal cutting block which can be of a known design with locator holes in which the locator pins can be received and a saw guide slot. The indicator block and the base instrument are removed from the joint space once the distal cutting block has been located on the femur. Removal of the base instrument involves releasing the control end of the femoral arm from the ratchet stay.

The arrangement of the femoral and tibial arms extending generally along the medial-lateral axis allows the steps of measuring the gap between the resected tibia and the femur in flexion, and of locating the plane for resecting the femur, to be carried out while the base instrument of the assembly of the invention is in place with the femoral and tibial plates in the joint space placing the joint under tension.

The invention claimed is:

1. An instrument assembly for use in a knee joint replacement surgery involving a knee joint, wherein the knee joint includes a tibia and a femur having medial and lateral compartments located on a medial-lateral axis that is transverse to an anterior-posterior axis, comprising:
  a base instrument that comprises:
    a tibial plate having a generally planar surface and an anterior edge;
    a femoral plate;
    a tibial arm having a plate end and a control end, wherein the tibial plate is fastened to the plate end of the tibial arm at its anterior edge, and wherein, when the tibial plate contacts the tibia, the tibial arm extends from the tibial plate in a direction generally parallel to the medial-lateral axis;

a femoral arm having a plate end and a control end, wherein the femoral plate is rotatably fastened to the plate end of the femoral arm, and wherein, when the femoral plate contacts the femur, the femoral arm extends from the femoral plate in a direction generally parallel to the tibial arm, and wherein the tibial arm and the femoral arm are pivotably connected to one another at a point between their respective plate and control ends so that pivotal movement of the femoral arm relative to the tibial arm changes a distance between their respective control ends; and an ancillary instrument, the ancillary instrument connected to the base instrument and positionable relative to the tibial plate in a direction parallel to the medial-lateral axis and in a direction parallel to the anterior-posterior axis when the tibial and femoral plates are in contact with the tibial and femur, respectively, and the tibial and femoral arms generally extend along an axis parallel to the medial-lateral axis.

2. The instrument assembly of claim 1, wherein the ancillary instrument and the base instrument have one of a spigot and a socket that can be used to connect one to the other.

3. The instrument assembly of claim 2, wherein the spigot is in the form of a plate and the socket is in the form of a slot wherein the plate can be received.

4. The instrument assembly of claim 2, wherein one of the spigot and the socket is provided on the tibial arm.

5. The instrument assembly of claim 1, wherein the tibial arm and the femoral arm are pivotably connected at a pivot pin extending generally along a line parallel to the anterior-posterior axis when the tibial and femoral plates are in contact with the tibia and femur.

6. The instrument assembly of claim 1, wherein the base instrument includes a locking device configured to lock the tibial arm and the femoral arm against the relative movement between the tibial arm and the femoral arm by reducing the distance between their respective plate ends.

7. The instrument assembly of claim 6, wherein the locking device includes a ratchet mechanism.

8. The instrument assembly of claim 1, further comprising a biasing device configured to act on the tibial arm and the femoral arm so as to reduce the distance between their respective plate ends.

9. The instrument assembly of claim 1, wherein the femoral plate has a pair of recesses formed therein configured to receive femoral condyles.

10. The instrument assembly of claim 1, wherein the femoral plate is fastened to the femoral arm such that the femoral plate may rotate to minimize differences in the forces that are applied across the medial and lateral compartments of the knee joint.

11. The instrument assembly of claim 1, wherein the ancillary instrument is selected from the group consisting of:
    a probe configured to contact the femur to measure a gap between the tibia and the femur;
    a cutting guide having a slot formed therein for receiving a blade of a saw or other cutting device; and
    a pin guide having at least one hole extending therethrough to define a location for a hole to be prepared in the femur.

12. The instrument assembly of claim 1, wherein the tibial plate includes a face that includes at least one projection for locating the tibial plate relative to the tibia.

* * * * *